(12) United States Patent
Welch et al.

(10) Patent No.: US 7,515,043 B2
(45) Date of Patent: Apr. 7, 2009

(54) PERSONAL STATUS PHYSIOLOGIC MONITOR SYSTEM AND ARCHITECTURE AND RELATED MONITORING METHODS

(75) Inventors: James P. Welch, Tigard, OR (US);
Steven D. Baker, Beaverton, OR (US);
Farzin G. Guilak, Beaverton, OR (US);
Anand Sampath, Streamwood, IL (US);
Daniel L. Williams, Norwell, MA (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 281 days.

(21) Appl. No.: 11/455,329

(22) Filed: Jun. 19, 2006

(65) Prior Publication Data
US 2007/0069887 A1 Mar. 29, 2007

Related U.S. Application Data

(60) Division of application No. 11/031,736, filed on Jan. 7, 2005, now Pat. No. 7,382,247, which is a continuation of application No. 10/806,770, filed on Mar. 22, 2004, now abandoned.

(60) Provisional application No. 60/554,706, filed on Mar. 20, 2004, provisional application No. 60/456,609, filed on Mar. 21, 2003.

(51) Int. Cl.
*G08B 1/08* (2006.01)
(52) U.S. Cl. .............................. 340/539.12; 340/539.1; 340/539.11; 340/573.1; 340/825.49; 340/825.69; 600/300; 600/301

(58) Field of Classification Search ............ 340/539.12, 340/539.1, 539.11, 539.13, 539.19, 539.26, 340/573.1, 825.36, 825.49, 825.69; 600/300, 600/301; 128/903, 920
See application file for complete search history.

(56) References Cited

U.S. PATENT DOCUMENTS 5,319,363 A 6/1994 Welch et al.
5,579,001 A 11/1996 Dempsey et al.

(Continued)

FOREIGN PATENT DOCUMENTS

WO 01/89362 A2 11/2001
WO 01/97686 A1 12/2001

OTHER PUBLICATIONS

International Search Report/Written Opinion (ISR/WO), Sep. 16, 2008, 7 pages.

*Primary Examiner*—Hung T. Nguyen
(74) *Attorney, Agent, or Firm*—Hiscock & Barclay, LLP (57) ABSTRACT

A method for communicating data using at least one network linking at least one respondent device with at least one monitoring device, said method comprising the steps of: continuously measuring at least one physiologic parameter for purposes of detecting a predetermined event using said at least one monitoring device; operating said network in an off state in which said network is off except for the periodic transmission of patient status data while said network is in a first operative state wherein said predetermined event has not occurred and transmitting said measured data along said at least one said network in a second state when said predetermined event has occurred.

14 Claims, 6 Drawing Sheets

U.S. PATENT DOCUMENTS

| | | | |
|---|---|---|---|
| 5,579,775 A | 12/1996 | Dempsey et al. | |
| 5,687,734 A | 11/1997 | Dempsey | |
| 5,748,103 A | 5/1998 | Flach et al. | |
| 5,767,791 A | 6/1998 | Stoop et al. | |
| 5,862,803 A | 1/1999 | Besson et al. | |
| 5,942,986 A | 8/1999 | Shabot et al. | |
| 5,957,854 A | 9/1999 | Besson et al. | |
| 6,198,394 B1 * | 3/2001 | Jacobsen et al. | 340/573.1 |
| 6,289,238 B1 | 9/2001 | Besson et al. | |
| 6,292,687 B1 | 9/2001 | Lowell et al. | |
| 6,440,067 B1 | 8/2002 | DeLuca | |
| 6,544,173 B2 | 4/2003 | West et al. | |
| 6,544,174 B2 | 4/2003 | West et al. | |
| 6,577,893 B1 | 6/2003 | Besson et al. | |
| 6,579,231 B1 * | 6/2003 | Phipps | 600/300 |
| 6,640,246 B1 * | 10/2003 | Gary et al. | 709/223 |
| 6,870,484 B1 * | 3/2005 | Brinsfield et al. | 340/825.49 |
| 7,215,991 B2 | 5/2007 | Besson et al. | |
| 2001/0023315 A1 | 9/2001 | Flach et al. | |
| 2003/0107487 A1 * | 6/2003 | Korman et al. | 340/573.1 |

* cited by examiner

PERSONAL STATUS PHYSIOLOGIC MONITOR SYSTEM AND ARCHITECTURE AND RELATED MONITORING METHODS

CROSS REFERENCE TO RELATED APPLICATIONS

This application is a divisional application of U.S. patent application Ser. No. 11/031,736, filed Jan. 7, 2005, now U.S. Pat. No. 7,382,247, which is a continuation application under 35 USC § 120 claiming benefit of U.S. Ser. No. 10/806,770, filed Mar. 22, 2004 now abandoned, which is a non-provisional patent application claiming priority under 35 USC §119 (e)(1) to U.S. Ser. No. 60/456,609, filed, Mar. 21, 2003, entitled "Personal Status Physiologic Monitor System and Architecture"and U.S. Ser. No. 60/554,706, filed Mar. 20, 2004, entitled "Personal Status Physiologic Monitor System and Architecture and Related Monitoring Methods", the contents of each of which are herein incorporated in their entirety.

FIELD OF THE INVENTION

This invention relates generally to patient monitoring systems, and more specifically to an improved patient monitoring system architecture.

BACKGROUND OF THE INVENTION

Over 1.1 million Americans experience a cardiac arrest each year. Of that number about 500,000 die, or about twice the number that die from any other cause, including accidents. Approximately half of these incidents occur within the hospital.

The first 4-6 minutes from the onset of cardiac arrest to treatment are crucial in obtaining a successful outcome. Therefore early detection, or better anticipation of the event is critical in positively impacting patient outcomes. Traditional methods for early detection are too costly to be broadly deployed. Current methods include continuous monitoring within the hospital setting through either fixed intensive care monitoring or ambulatory telemetry monitoring. The capital cost of current technology is approximately $12,000 to $30,000 per device and requires high technical skill levels to use the devices and related systems effectively.

Continuous vital signs monitoring systems are well known to those skilled in the art. Hospitals have broadly adopted such systems in the early 1960s as intensive care units emerged as a standard of care. These early systems utilized proprietary network connectivity from a plurality of bedside monitors to a central viewing station. Early systems were based on both hardwired analog and digital communications methods. These systems migrated to standards based IEEE 802.3 Ethernet-based digital communications systems in the 1980s, as Ethernet technologies matured and became cost effective to implement. Hardwired systems expanded in the hospital as medical care subspecialties grew, but were generally restricted to intensive care settings.

Concurrent with the development and growth of hardwired systems, one-way telemetry systems were created that allowed ECG monitoring of patients during ambulation. Early systems emerged from NASA development in the early '60s for monitoring of astronauts. Simple analog radios operating in the unused VHF and UHF spectrum with simple modulation schemes grew in coronary care step-down units. These systems operated under Part 15 of the FCC Rules in unused portions of the television spectrum.

Telemetry technology improved with one-way digital communications in the 1980s. Additional parameters were added, first by Siemens in adding blood oxygen saturation ($SPO_2$) and then by others in the late 1980s.

In 1992 Welch, et al., patented for the first time a system that allowed central surveillance monitoring to be decoupled from intensive care or coronary care step down environments. This patent, U.S. Pat. No. 5,319,363, allowed central surveillance to be accessible to any bedside location without dedicating devices to these beds. The '363 patent further provided for both two-way hardwired and wireless communications methods. Protocol Systems, Inc., later acquired by Welch Allyn, Inc. of Skaneateles, N.Y., commercialized this invention.

In terms of other known prior art, Dempsey, U.S. Pat. Nos. 5,579,001, 5,579,775 and 5,687,734 each describe a two-way telemetry apparatus that uses a backchannel receiver to carry control signals between a proprietary wireless network and a bedside monitor. Additionally, Dempsey further describes a system apparatus that combines traditional one-way medical telemetry and traditional one-way (opposite) paging systems to achieve bi-directional communications. Flach, et al., U.S. Pat. Nos. 5,767,791 and 5,748,103, describe a combined bidirectional telemetry system that optimizes available bandwidth with modulation schemes such as frequency hopping. VitalCom, later acquired by GE Medical Systems, has since commercialized the subject matter described by this latter patent.

West, et al., U.S. Pat. Nos. 6,544,173 and 6,544,174, improved upon the Welch '363 patent describing a two-way standards based wireless patient monitor and system that provides connectivity to a plurality of central stations in an enterprise wide real-time monitoring network. The West patents also describe a patient wearable device that can be configured in either a connected state or a non-connected state.

Besson et al., U.S. Pat. No. 5,682,803, describes a wireless two-way sensor with error correcting means that can be used to control and manipulate the data communicating between a patch electrode and a bedside monitor. Besson's intent was to eliminate the wires between sensors and bedside monitors.

DeLuca, U.S. Pat. No. 6,440,067B1, describes a system that includes body worn sensors communicating to a body worn repeater which in turn communicates to a base station for transmission over a telephone line or internet to a central review station. DeLuca's device is designed for the monitoring of physical activity that is associated with a specific "non-communicating" activity.

All of the above known references, and others as referenced that are referenced by these patents, commonly describe a real time, continuous physiologic monitoring system. The devices described by each of these patents are intended to be in a continuous connected state when configured with an associated system. The consequence of this requirement is a network that requires sufficient power to support a continuously connected instrument. Therefore, for wireless connectivity, sufficiently sized batteries must be incorporated in order to achieve acceptable useful life for the combined apparatus.

The above noted '803 Besson patent and its progeny is especially aware of this requirement and teaches means for powering wireless sensors to support the sensor and the wireless link. Besson et al. further provides error correcting means, as well as control and manipulation of the communications data, in order to achieve high data throughput quality at minimum RF power levels. DeLuca also recognizes this limitation and provides for recharging means for his described body-worn sensors.

Therefore, there is a general need in the field for a low cost, simple to use diagnostic monitoring device. The potential market for such a device goes well beyond the more than 61 million Americans who are classified as having some form of cardiovascular disease. The US military is also actively investigating personal status monitoring for its deployed military personnel. Military sources estimate an annual volume of 40,000 units. It is a therefore primary object of the present invention to address the above-noted need in the diagnostic field.

SUMMARY OF THE INVENTION

According to one aspect of the present invention, there is disclosed a system for actively monitoring a patient, said system comprising:

at least one body-worn monitoring device, each said at least one body-worn monitoring device including at least one sensor capable of measuring at least one physiologic parameter and detecting at least one predetermined event;

at least one intermediary device linked to said at least one body-worn monitoring device by at least one network; and at least one respondent device linked to said at least one intermediary device by at least one network and programmed to perform a specified function automatically when said predetermined event is realized. According to at least one embodiment, at least one of the at least one body-worn monitoring device, at least one intermediary device and at least one respondent device is programmed to perform a specific function automatically when the predetermined event occurs, without user intervention. For example, the at least one respondent device can be programmed to contact emergency services upon occurrence of the predetermined event.

According to another aspect of the present invention, there is disclosed a system for actively monitoring a patient, said system comprising:

at least one body-worn monitoring device, each said at least one body-worn monitoring device including at least one sensor capable of measuring at least one physiologic parameter and detecting at least one predetermined event;

at least one intermediary device linked to said at least one body-worn monitoring device by at least one network;

at least one computer linked to at least one intermediary device by at least one network; and at least one respondent device linked to said at least one computer through at least one network, at least one of the body-worn monitoring device, said at least one intermediary device and said at least one respondent device being programmed to perform a specified function automatically when said predetermined event is realized. The computer can, for example, be a server that can also permit transmission of control algorithms through the at least one network to the body-worn monitoring device for event detection.

According to yet another aspect of the present invention, there is provided a system for actively monitoring a patient, said system comprising:

at least one body-worn monitoring device, each said at least one body-worn monitoring device including at least one sensor capable of measuring at least one physiologic parameter and detecting at least one predetermined event;

at least one intermediary device linked to said at least one body-worn monitoring device by means of a first wireless network; and at least one respondent device linked to said at least one intermediary device by a second wireless network wherein at least one of the body-worn monitoring device, said at least one intermediary device and said at least one respondent device is programmed to perform a specified function automatically when said predetermined event is realized. In one embodiment, the first wireless network is a local low-power personal area network and the second wireless network is a wide area network or equivalent.

According to yet another aspect of the present invention, there is described a system for actively monitoring a patient, said system comprising:

at least one body-worn monitoring device, each said at least one body-worn monitoring device including at least one sensor capable of measuring at least one physiologic parameter and detecting at least one predetermined event;

at least one intermediary device linked to at least one body-worn monitoring device through a first wireless network; and and at least one respondent device linked to said at least one intermediary device through a second wireless network, wherein at least one of said at least one body-worn monitoring device, said at least one intermediary device and said at least one respondent device is programmed to perform a specified function automatically when said predetermined event is realized.

According to still another aspect of the present invention, there is disclosed a system for actively monitoring a patient, said system comprising:

at least one body-worn monitoring device, each said at least one body-worn monitoring device including at least one sensor for measuring at least one physiologic parameter and detecting at least one predetermined event;

at least one intermediary device lined to said at least one body-worn monitoring device by means of a first wireless network;

at least one computer linked to said at least one intermediary device by a second wireless network; and at least one respondent device linked to said at least one computer by said second wireless network, at least one of said at least one body-worn monitoring device, said at least one intermediary device and said at least one respondent device being programmed to perform a specified function automatically when said predetermined event is realized.

According to yet still another aspect of the present invention, there is disclosed a system for communicating data, said system comprising:

at least one monitoring device, said at least one monitoring device having at least one sensor for continuously measuring at least one physiologic parameter and detecting at least one predetermined event;

at least one network linking said at least one monitoring device to at least one respondent device wherein said at least one network is normally operatively in a first state where the network is off except when periodic data is transmitted, said network having a second state where data is transmitted upon said at least one predetermined event having occurred. The periodic data can be compressed data or portions of a measured physiologic data stream.

According to yet another aspect of the present invention, there is disclosed a method for performing patient to device context management, said method comprising the steps of:

producing a physiologic signal, as detected by a monitoring device;

associating a unique monitoring device identifier to a unique patient identifier; and appending said unique patient identifier to said continuous physiologic signal, wherein a change in said physiologic signal in which said signal is no longer continuous will cause the unique patient identifier to disassociate from said signal.

According to still another aspect of the present invention, there is disclosed a method for performing patient to environment context management comprising the steps of:

producing a continuous physiologic signal, as detected by a monitoring device;

associating a unique monitoring device identifier to a unique patient identifier;

appending said unique patient identifier to said continuous physiologic signal; and associating a unique location device identifier to at least one unique monitoring device identifier, thereby associating a patient location to at least one unique patient identifier.

According to yet another aspect of the present invention, there is disclosed a system for actively monitoring a patient, said system comprising:

at least one ECG monitoring device;

at least one computer for receiving data from said ECG monitoring device; and at least one network linking said at least one ECG monitoring device and said at least one computer in which said at least one ECG monitoring device transmits all the R-R intervals to said at least one computer regardless of whether said at least one ECG monitoring device is transmitting ECG waveforms or not.

According to still another aspect of the present invention, there is disclosed a method for balancing power consumption, sensitivity and specificity in detecting physiologic events, said method comprising the steps of:

determining the power consumption as a function of sensitivity and specificity for each computational element of the system;

arranging the computational flow from the most power sensitive of said computational elements to the least power sensitive of said computational elements;

setting the sensitivity of the first computational element to allow detection of all events; and sending the events detected along with an associated at least one waveform by the first computational element to the second computational element; setting the sensitivity of the second computational element to identify at least some of the false positive detections received from said first computational element.

It is believed that the presently disclosed system architecture distinguishes itself from that of the prior art by uniquely utilizing two-way radio and technology and advanced signal processing. This architecture is based on a communications network that is predominantly in an "off" state when the at least one predetermined event has not occurred. That is, there is no requirement for continuous monitoring outside of the physiologic sensors. This innovation permits the presently described system to share wireless network resources with other applications without the need to install dedicated wireless network equipment. The system which can preferably include, for example, at least one body-worn personal status monitoring device, communicates to an intermediary personal gateway device that is also preferably patient-worn and uses a WiFi, IEEE 802.11b, or other emerging standards-based radio network (such as, for example, IEEE 802.11a or IEEE 802.11g) that is already installed in the facility, or communicates to a respondent device such as a cellular phone or at least one other respondent device using TDMA, CDMA, GSM, G3 or other WAN (Wide Area Network) communications technologies.

Preferably, the personal status monitoring device of the present invention contains advanced signal processing algorithms that are designed to detect events, rather than continuously streaming patient-related vitals data over the wireless networks. A beacon using the same wireless communications means as is used to transfer physiologic data on the personal status monitoring device maintains a connectivity status that is independent of event driven transmission. Embedded in the beacon are vital signs status data and signal processing data that can efficiently reconstruct significant information sensed by the at least one physiologic sensor. The data representation is preferably be lossy (as opposed to the lossless forms that are presently found in the current art). Alternatively, the embedded beacon may contain a subset of the physiologic data necessary to maintain a continuous record, such as, but not limited to heart rate and R to R intervals, depending in part on data compression capabilities that are contained within the personal status monitoring device.

Advantageously, the personal status monitoring device of the present invention is preferably designed to achieve low purchasing costs and as a result may not contain sufficient processing power to complete the signal analysis function that would be required for medical personnel interpretation. Therefore, signal processing is preferably distributed throughout the herein described system. By distributed, it is meant that the personal status monitoring device is highly sensitive in its event identification. Additional signal processing algorithms and pattern recognition may then be embedded in at least one intermediary device (e.g., a personal gateway device, and/or central server) and/or respondent devices for the purpose of reducing false alarms and reducing data to that of useful clinical information wherein the sensitivity is adjusted in each succeeding device to identify false positive detections received therefrom.

To Applicants' best knowledge, it is believed that there are no existing systems known that provide system features as described by the present invention. That is to say, existing all known WLAN systems used for medical monitoring are used in a continuous "ON" state in which data is continually or continuously transmitted through the system regardless of the condition of the patient. Existing WLAN non-medical systems are not used for event based surveillance monitoring with a beacon feature in order to maintain connectivity status. It is believed that no system used today provides lossy physiologic data reduction in order to achieve low power consumption for communications. Furthermore, it is believed that no existing system provides distributed signal processing and pattern recognition in order to optimize low power and normally "OFF" or quiet communications optimization.

An advantage of the present invention is that the unique network architecture features described herein preserves battery life by minimizing the use of any wireless (e.g., RF) links between at least one personal status monitoring device and at least one intermediary device (such as a personal gateway device according to the preferred embodiment), as well as between the at least one intermediary gateway device and the wireless network infrastructure. This feature allows the monitoring and intermediary (e.g., gateway or other) devices to embed smaller batteries, such as, for example, those found in digital wrist watches, and therefore smaller packages that lend themselves to lower cost platforms can be more integrated into a normal patient activity level.

A further essential advantage of the present invention is that the ubiquity permits the personal status monitoring device of the present invention to assume other functions, such as, for example, context management. By context management, it is meant that the binding of a patient or other type of unique identifier that can be embedded into the personal status monitoring device of the present invention upon installation of same on the patient's body can also be used for positive identification of the patient, independent of the device's primary personal status monitoring function. Healthcare workers can therefore query the personal status monitoring device for patient identification with the same respondent device used for event monitoring.

Additionally, the system permits other forms of context management, for example, between the patient and the environment in order to associate patient location with a patient identifier.

These and other objects, features and advantages will become readily apparent to those of sufficient skill when read in conjunction with the accompanying drawings.

DETAILED DESCRIPTION

The following description relates to an event monitoring systems architecture according to a preferred embodiment of the present invention. Certain terms are used throughout the discussion, such as, for example, "top", "bottom", "upper", "lower" and the like in order to provide a convenient frame of reference with regard to the accompanying drawings. These terms, however, unless specifically indicated otherwise, are not intended to be over limiting of the present invention.

Throughout the course of the discussion, various terms are used that require additional definitions for clarity.

By "body-worn device," it is meant that the device is entirely worn on the body of the patient wherein the device is affixed or otherwise attached directly to the skin of the patient.

"Network" refers to a communications linkage between at least two devices. Unless stated otherwise, this linkage can be wireless or hardwired in nature or both.

A "patient-worn" device refers to a device that is carried by or is attached to a patient. A patient-worn device according to this definition can include but is not limited to a "body-worn" device.

An "intermediary device" refers to a device such as a relay radio link, a computer or other apparatus that is disposed between at least one patient monitoring device and at least one respondent device.

"Respondent device" refers to a device that is notified of a predetermined event in accordance with the present system. The respondent device can be a cellular phone, a computer, or other device that can further be enabled to be accessed by a user to gain access to the present system, request data, input patient-related data and other functions.

Figure 1:
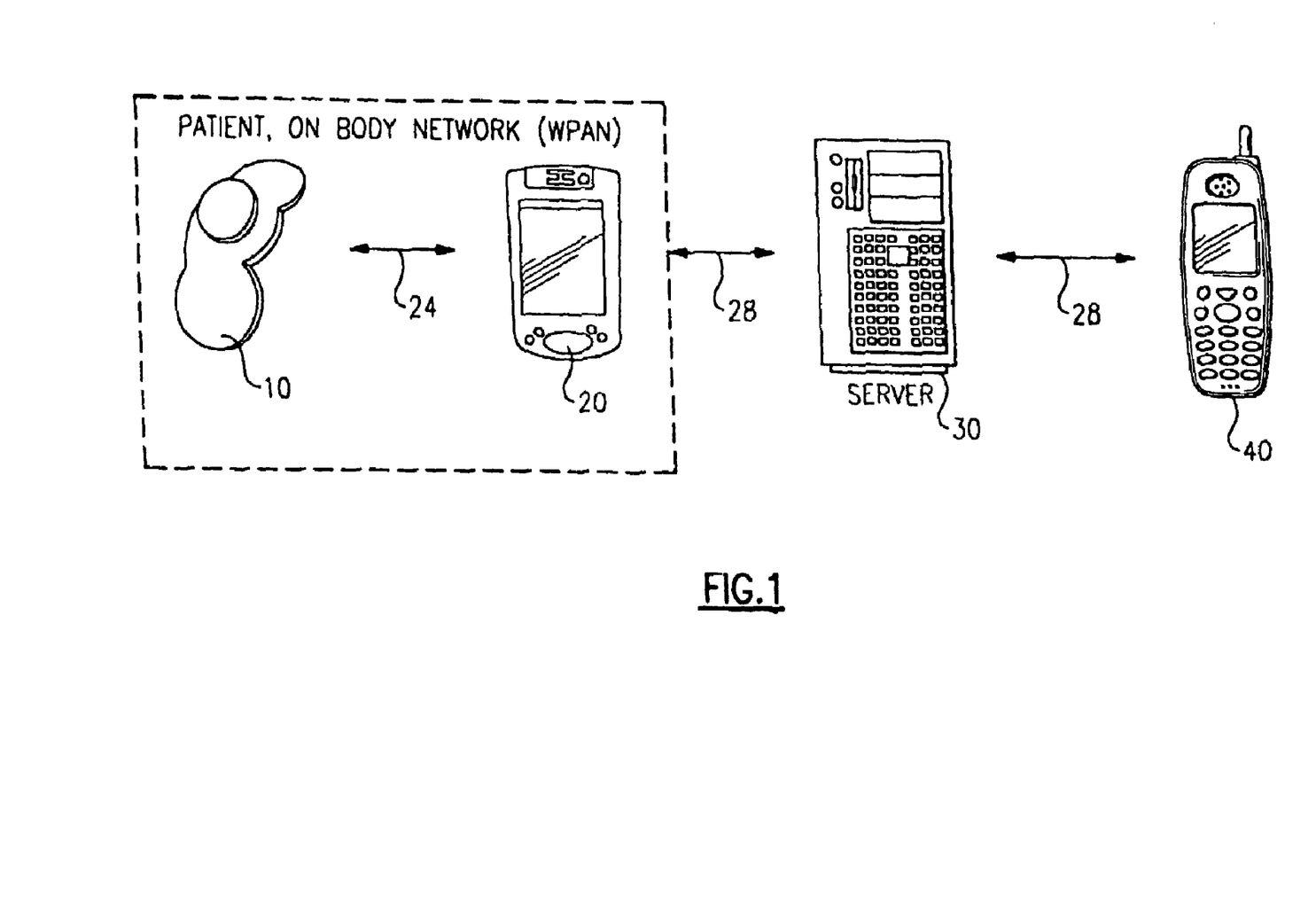
FIG. 1 is a simple diagrammatic view of the primary components of an event monitoring system in accordance with a preferred embodiment of the present invention.

In brief, the present invention is a systems solution for the early detection and communication of life threatening physiologic events to appropriate first responders. Referring to FIG. 1, the fundamental architecture of the herein described system includes four (4) primary components:

1) at least one low cost, ultra-low power (e.g., long battery life), easy to use personal, body-worn status monitoring device 10 that is attached directly to the patient;

2) at least one wireless, battery powered, intermediary or personal gateway device 20 that is patient-worn, such as on the arm, a belt or otherwise disposed. The at least one personal gateway device 20 according to this particular architecture is used to relay events, signals, and information, preferably bi-directionally between the attached personal status monitoring device 10 and a central server 30;

3) a central server 30 that provides a plurality of database management, rule sets, advanced signal processing and display rendering, with regard to the above noted system components, as well as information routing to at least one respondent device; and 4) at least one respondent device 40 that displays pertinent information regarding patient status. Additional details relating to each of these system components is provided below.

Figure 2:
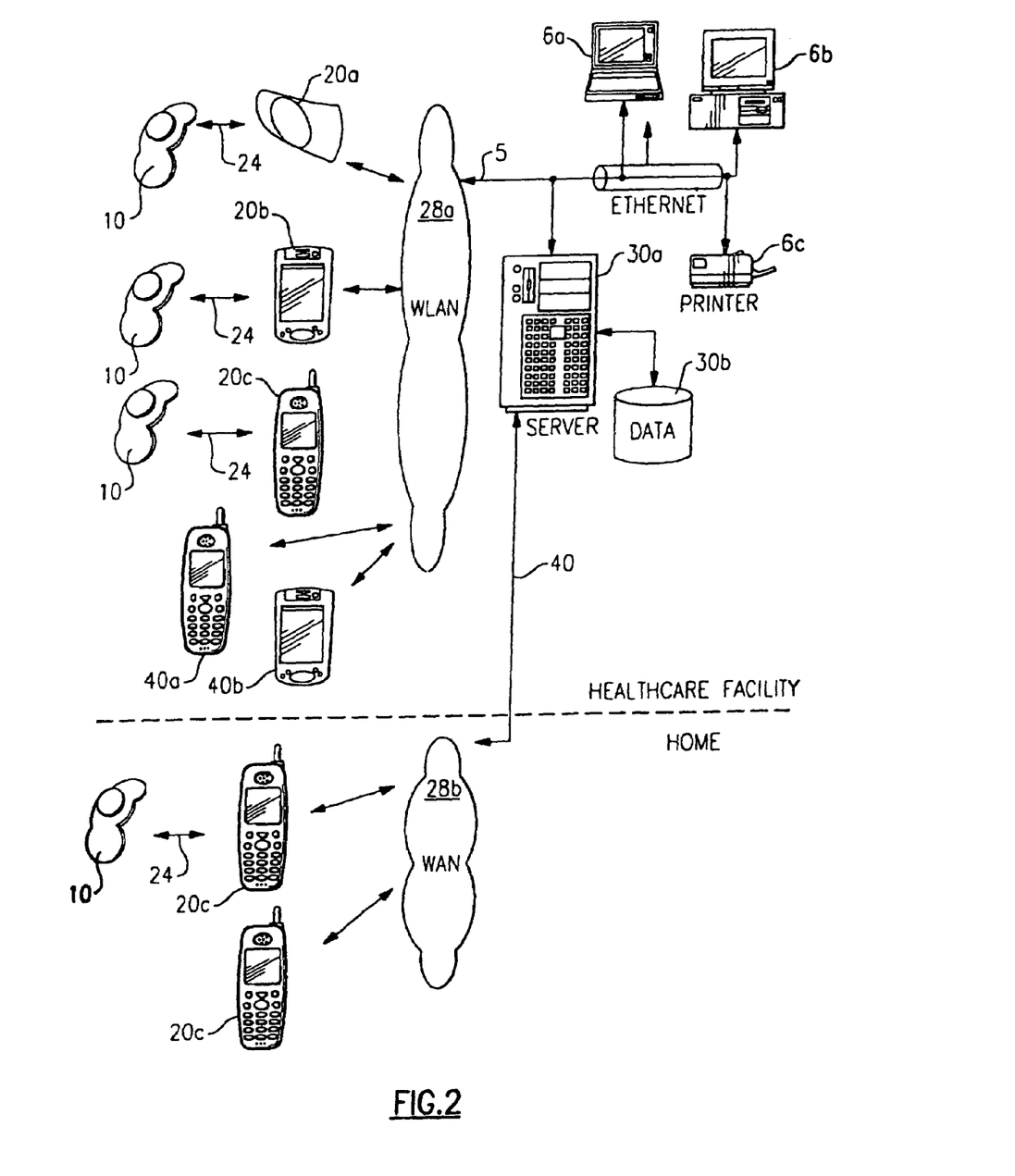
FIG. 2 is a diagrammatic view of a preferred system/network architecture of the present invention.

Referring to FIG. 2, the wireless connectivity architecture of the present embodiment that includes the above primary system components is preferably defined by two separate wireless networks; namely:

i) a low power Wireless Personnel Area Network (WPAN) 24 having an effective range of about 1-10 meters; and ii) a medium/long range wireless network 28 that is preferably based on a Wireless Local Area Network (WLAN) technology (e.g., IEEE 802.11x), a Wireless Area Network (WAN) (e.g., cellular phone networks) or both.

It should be noted that the above system construction is preferred for the sake of power consumption and feasability. It should be pointed out, however, that there are many variations that can be utilized herein. For example, according to one variation, the server can be removed in favor of an arrangement that includes a personal status monitoring device, an intermediary device such as a computer and a respondent device in which the respondent device is configured in the manner of a computer. According to yet another variation, the intermediary device can be entirely removed from the system and a single wireless network can be utilized in lieu of the two separate wireless networks described herein. Similarly and for reasons described below, the system is not specifically limited necessarily exclusively to the use of wireless networks. That is, some hard wired connections could be contemplated within the inventive concepts herein.

Still referring to FIG. 2, the present monitoring system is defined by a distributed hardware, networked and logical architecture leveraging low cost, broadly applied technologies. As previously noted, the four (4) major or primary components of the present system/network architecture includes at least one personal status monitoring device 10; at least one personal gateway or intermediary device 20a, 20b, 20c; at least one central server 30a, having a database 30b; and at least one respondent device 40a, 40b. The intermediary or gateway device 20 can be a body-worn device such as shown in 20a, a PDA 20b, a cellular phone 20c, or other similar device acting predominantly as a radio intermediary or relay to the server 30a, such as a PAN to TCP/UDP translator.

The server 30a can be provided in a separate connection to other devices such as a laptop computer 6a, an IBM or other compatible computer 6b and at least one printer 6c such as through an Ethernet connection there with as found in a healthcare facility. At least one respondent device is represented by a cellular phone 40a and a PDA 40b though other devices such as a computer can be utilized. As shown, the WAN 28(*b*) provides a server 30a input for home use of the patient status monitoring device 10 via the local network 24 through an intermediary device (cellular phone 20c).

A fundamental assumption of the present monitoring system is that each of the herein described central server 30a, the intermediary devices 20a, 20b, 20c and the respondent devices 40a, 40b and therefore the system as a whole, normally is predominantly in an "off" or "quiet" state, in spite of the fact that the at least one personal status monitoring device 10 may be continuously sampling physiologic signals from the patient as well as environmental signals, and is processing these signals for specific events. The use of this "quiet" state is in direct contrast with traditional hospital based continuous monitoring systems and is an essential feature of the herein described system.

Additionally, patient context management is an essential task of the herein described system that is effectively managed through the at least one personal status monitoring device 10. In brief, a unique hardware (HW) ID 209, 524, FIGS. 3, 4, respectively, of each of the gateway device and the patient status monitoring device are associated with a unique patient identifier 206, FIGS. 3, 4, respectively, and this unique patient identifier is then appended to the continuous physiologic signal as detected by the personal status monitoring device 10 that is transmitted to the at least one personal gateway device 20a, 20b, and 20c, thereby creating a binding relationship. This "binding" relationship exists for as long as the personal status monitoring device 10 maintains a positive continuous physiologic signal relationship with the patient. Any disruption in continuous signal recognition for a prescribed length of time will result in an "unbound" state that will remove the unique patient identifier from the patient status monitoring device 10.

In a preferred form, each of the personal status monitoring device 10 and the personal gateway device 20 are first synched to one another. This synching can occur either on the patient or not. Hardware IDs 209, 524 (shown in FIGS. 3, 4, respectively) for each of the two devices 10, 20 are then transmitted to the central server 30a and the unique patient identifier 206 is created and transmitted for storage by the personal status monitoring device 10 and for appending to the measured physiologic signal. Similarly, the intermediary or gateway device 20 can also store the unique patient identifier 206. This appended patient identifier 206 is found in each transmission data packet transmitted by the radio of the patient status monitoring device as a periodic beacon. The unique patient identifier 206 is an unique number or other symbol and therefore not the name of the patient. Unbinding of this identifier 206, caused for example by the monitoring device inadvertently detaching from the patient, will then disable same, for example, from being used by another patient.

Figure 3:
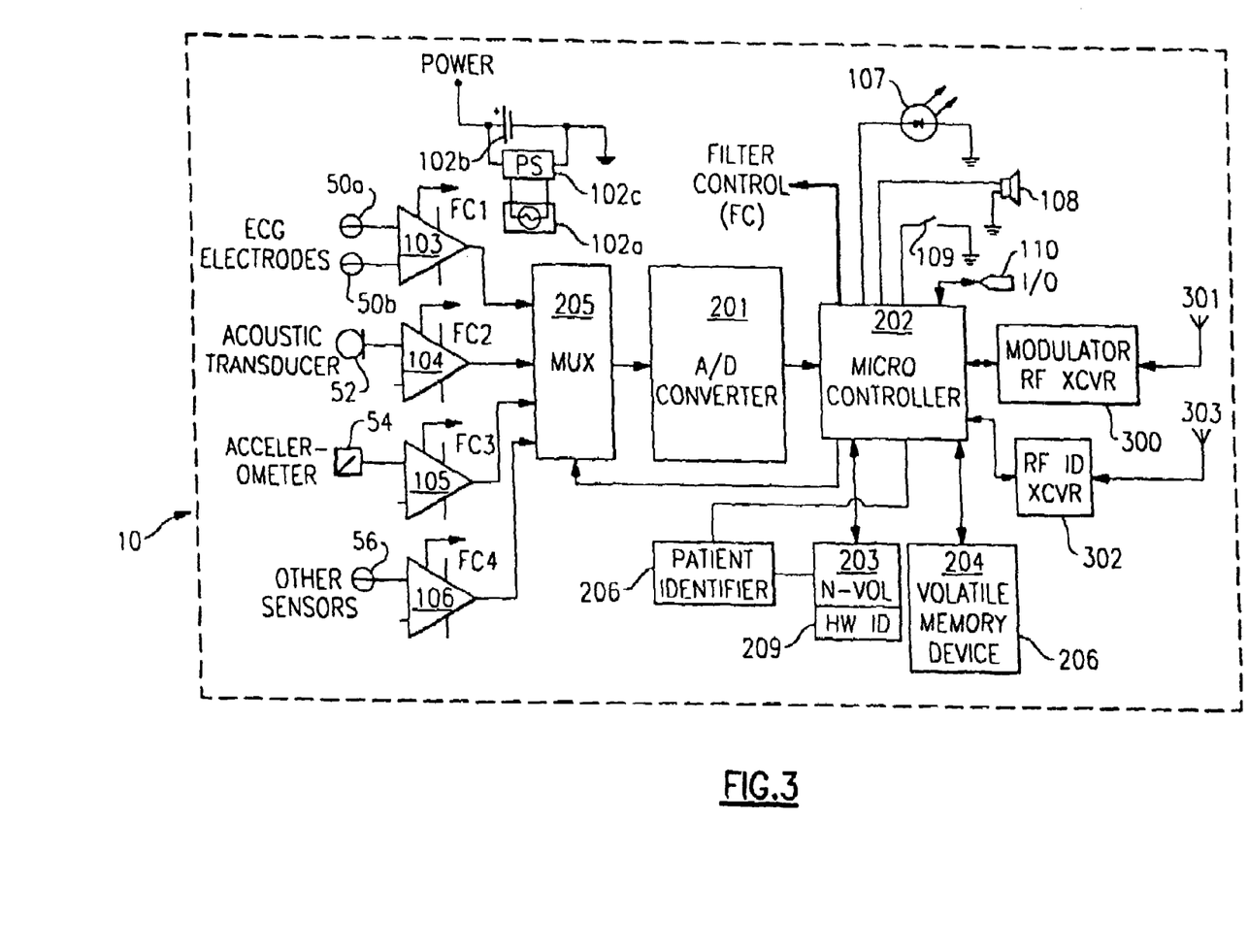
FIG. 3 is a schematic diagram of a personal status monitoring device component of the system depicted in FIGS. 1 and 2.

With the preceding overview providing cursory background, a more detailed description is made with regard to each of the above primary system components, starting with the personal status monitoring device 10. Referring to FIGS. 2 and 3, the personal status monitoring device 10 is a patient wearable device, and is preferably encapsulated in a single flexible covering 14. This device 10 is preferably self-contained and includes a plurality of components, including a plurality of electrodes and/or physiologic sensors that are integrated into the highly flexible covering 14 for attachment directly to the skin of the patient, thereby making the device "body-worn". Personal status monitoring devices 10, as noted below, may contain one or more instrumentation applications depending on the desired measurement(s). Such measurements can include, but are not limited to, ECG, acoustics, tissue and blood oxygen levels, blood chemistry, surface or body temperature, and accelerometry (e.g., patient movement or determination of patient orientation) with each application being designed for low power utilization. For example and according to one application, a plurality of personal status monitoring devices 10, each having unique functionality with regard to a particular patient, can be positioned on the patient simultaneously at any number of locations that optimize physiologic signal acquisition. These locations may or may not be immediately proximate to one another on the patient.

Referring to FIG. 3, an appropriate schematic diagram of a preferred embodiment of the personal status monitoring device 10 is depicted. In the present embodiment that is described throughout, the personal status monitoring device 10 includes a disposable ECG electrode assembly, though it should be realized that the device can include both disposable as well as reusable or semi-reusable (e.g., single patient) instrumentation assembly in whole or at least in part. According to this figure, the ECG assembly includes a pair of ECG electrodes 50a,b that are connected to an analog ECG front end 103, the front end preferably including pacemaker detection, such as is generally known to those in the art. The physiologic and measuring parameters of the patient-worn status monitoring device 10 described herein include one channel of ECG measurement using two or three or more electrode configurations. Two electrodes are shown according to this embodiment, as well as one additional channel of acoustic signal and one additional channel of accelerometry, having respective front ends 104, 105. Additionally, the personal status monitoring device 10 further includes scalability, thereby permitting additional channels, such as for determining other parameters including but not limited to body temperature, pulse oximetry, patient location and/or other parameters to be added. The ECG front end 103 is connected to a multiplexer 205 that samples ECG as well as other signals integrated into the personal status monitoring device 10. Alternatively, a plurality of A/D converters may be used. In the case in which only one ECG vector is measured by the personal status monitoring device 10 only, the multiplexer 205 would not be required.

An A/D converter 201 converts the analog signal from the various sensors and electrodes into digital values for manipulation, and analysis by a contained microcontroller 202. The Propaq 100 series vital signs monitor manufactured by Welch Allyn, Inc., for example, serves as one reference design. All or some of these components may be integrated into a single integrated systems semiconductor, as is found in many families of microcontrollers. The microcontroller 202 in turn may also be available on the radio semiconductor, such as an ASIC chip.

The microcontroller 202 further provides the features of signal processing, as well as feature and event extraction of the ECG signal for wireless relay through an RF radio transceiver 300 to a corresponding RF antenna 301 to the intermediary gateway device 20, FIG. 1 via the first wireless network 24, FIG. 1. The microcontroller 202, RF radio transceiver 300 and RF antenna 301 may be a single semiconductor or alternatively can be designed as individual components. Furthermore, the microcontroller 202 can alternatively be divided into two microcontrollers; that is, a first microcontroller (not shown) for instrumentation data acquisition and reduction, and a second microcontroller (not shown) used only for radio communications. A further design permits one-way or two-way (e.g., bi-directional) communications with the first and second microcontrollers.

Still referring to FIG. 3, non-volatile memory device 203 and volatile memory device 204 may be integrated into the microcontroller 202 or be separately provided. Non-volatile memory device 203 preferably includes a re-writable memory component, such as FLASH or a similarly utilized technology, and a non-rewritable memory component, such as PROM (Programmable Read Only Memory), for the storage of data and configuration information, such as patient name, ID, care plan, and/or other information that is specifically and categorically unique to the patient as described below. Input of any or portions of this information and data may be entered either though the RF antenna 301 and RF radio transceiver 300 noted above, an RFID antenna 303 and an RFID radio transceiver 302 or through a separate input/output I/O port 110.

The presently defined system is versatile and anticipates many different forms of patient identification. For example, patient identification in healthcare hospital practice typically includes a unique alphanumeric number that is printed onto a wrist strap or similar type of bracelet that is worn by the patient during their hospital stay. Some hospitals, alternatively or in combination, place bar codes on these straps for machine readability. Yet another alternative method of patient identification is to embed a low cost RFID device directly into the wrist strap. The present system architecture is designed to transfer this information, regardless of the manner of patient identification, either through an auxiliary detection device (e.g. a bar code scanner (not shown) having a radio transmitter that is compatible with the personal status monitoring device 10 or directly, as in the case of an embedded RFID tag on the same patient as that of the personal status monitoring device 10. The auxiliary detection device can further be connected indirectly with the server 30 in the network, for example via the personal gateway device 20.

In addition to patient identification, a unique device or hardware identification is stored in non-volatile memory device 203, this storage being done preferably at the time of manufacture and being done in the non-rewritable memory component thereof. In terms of labeling, appropriate regulatory labels are utilized. Moreover, a clearly visible unique product identifier (e.g., serial number) is also preferably encoded in machine and human readable formats (such as, for example, bar code) on the exterior of the personal status monitoring device 10.

Figure 4:
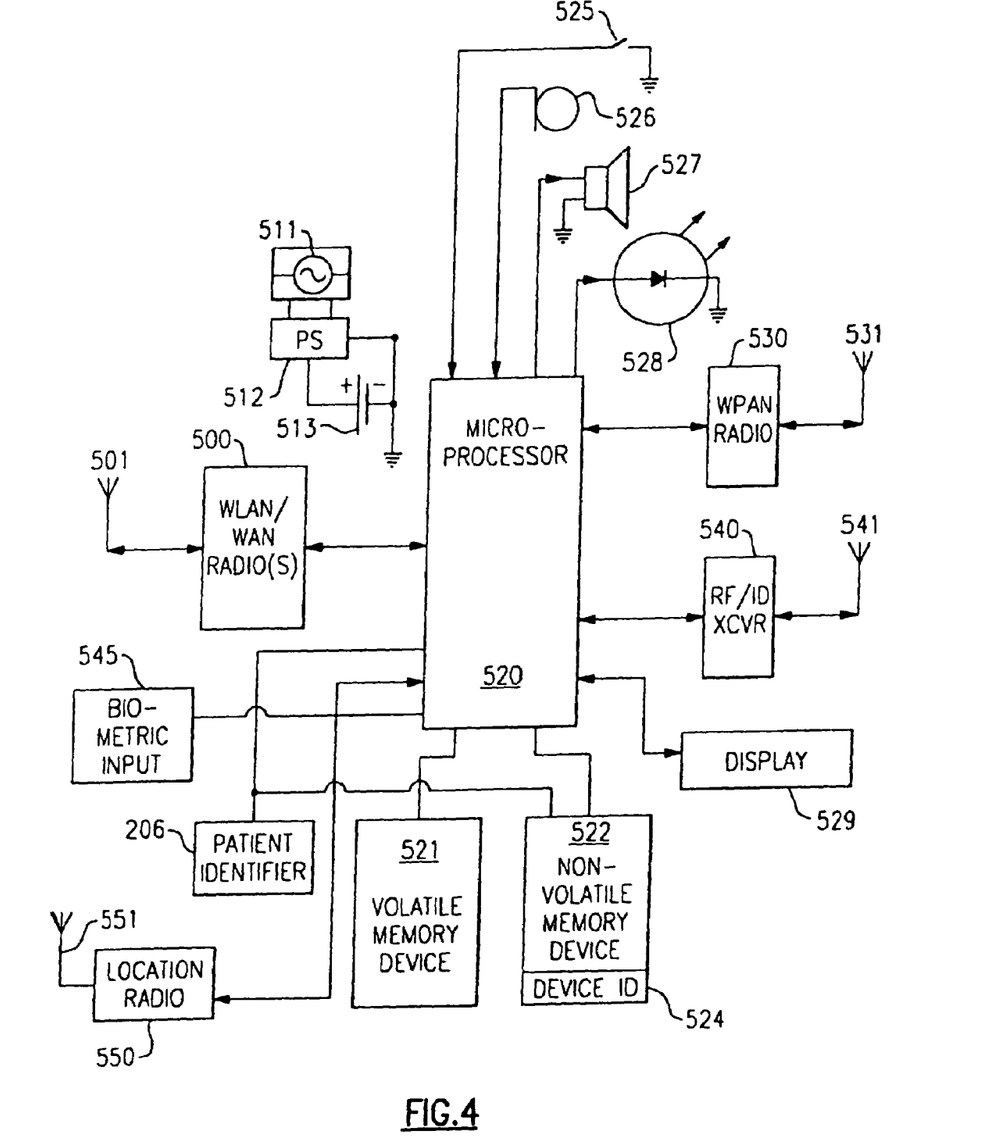
FIG. 4 is a schematic hardware diagram of a preferred personal gateway or intermediary device component of the system/network shown in FIGS. 1 and 2 of the present invention.

Data storage can generally be accomplished in the personal status monitoring device 10 as follows:

First, once respective hardware IDs 209, 524, FIGS. 3, 4, respectively, and a patient ID have initially been established at the device level (e.g., the gateway device/personal status monitoring device interface), each of these are transmitted to the server 30 and a unique patient identifier 206 is created. This identifier 206 is relayed via the WLAN 28 to the gateway device 20 and then to the personal status monitoring device 10 for storage. This storage, unlike the hardware identification occurs in the non-volatile memory device within the re-writable memory component thereof. As a result of the preceding, no encryption is required of patent data subsequently transmitted in that the unique patient identifier 206 is known only to the server 30.

Derived sensor data is also stored into the nonvolatile memory devices 203 of the microcontroller 202 of the personal status monitoring device 10. This data includes a sample (e.g., on the order of approximately 6-12 seconds) of digitized waveform data, as well as storage of selected compressed data.

As noted, context management is an essential task of the personal status monitoring device 10. Fusion occurs between the hardware ID 209, 524, FIGS. 3, 4, respectively, the unique patient identifier 206, and the derived sensor data (e.g., a continuous physiologic signal) wherein decay or removal of fusion in absence of continuous sensor data causes the binding of the patient identifier 206 to cease. Absence of continuous sensor data can occur in a number of different ways, for example, when the battery of the personal status monitoring device 10 is low or dead, when the intermediary gateway device 20 is out of range from the personal status monitoring device 10 in the personal area network 24, when electrode leads from the personal status monitoring device 10 have come loose or have detached from the patient, or based on a specific command of the central server 30.

Still referring to FIG. 3, a number of optional sensors 56 can also be connected to the microcontroller 202 of the personal status monitoring device 10 for additional functionality. In addition, a number of optional actuators can also be added thereto. These actuators contain a number of output functions such as and including visual annunciation 107, audio annunciation 108 and/or user actuation 109 that can also be connected in like manner. These annunciators 107, 108, 109 can be used for a variety of purposes including, but not limited to, device operation and state indication, alarm and/or alert event, user attention indication, and user request for attention, among others.

Optional means associated with the personal status monitoring device 10 are further provided for the recharging of an embedded battery 102b through mechanical, inductive, or thermal charging mechanisms 102a, such as those presently found, for example, in digital watches via a power supply circuit 102a. In the instance in which portions of the personal status monitoring device 10 are disposable, some or all of these recharging means 102a, may not be necessarily required and a disposable battery can be utilized.

Still referring to FIG. 3, a series of amplifiers located in front ends 103, 104, 105, 106 may preferably include selectable or tunable filters for the removal of environmental or other unwanted signals. More detailed discrete circuits may alternatively be utilized in lieu of the amplifiers 103 as is commonly known in the field and require no further discussion herein. Provisions for the control of the amplifiers 103, 104, 105, 106 are provided through ports (not shown) that are provided on the contained microcontroller 202. As previously stated, other biomedical signals may also be included in the same or similar path to provide similar functionality hereindescribed of the device 10.

As noted above and in addition to the ECG electrode assembly an acoustic channel is provided, whereby any predetermined number of acoustical transducers, for example, electret or piezo or other suitable sensors 52, can be used to in order detect audible biomedical signals for measurement and event detection and transmission. In addition and according to this embodiment, an accelerometry channel is also provided that includes at least one accelerometer 54 for measuring patient movement for determining body orientation, activity and critical events, such as an unexpected fall. Sensitive three-axis accelerometers may also be incorporated into the flexible covering 14 of the monitoring device 10 for mechanically detecting heart beats on the surface of the chest or respiration rate through low frequency chest wall motion. Other biomedical measurements may be suitably added, such as tissue and blood oxygen levels, as low power instrumentation solutions become available. These additional measurements can be formed either internal to the overall package or on the flexible covering 14.

At least one patient location sensor (not shown) can be additionally integrated into the personal status monitoring device 10 by leveraging the network infrastructure with the radio technology as is generally known to those skilled in the art of IEEE 802.15.4 technology or other location technologies, such as those offered by Radianse Corp. Radiolocation technology can therefore be fused to patient identification in order to provide unique patient location within facilities that are equipped with this capability.

As noted above, one primary purpose of the herein-described system is to continuously monitor the status of the person to which a personal status monitoring device is attached based on one or more physiologic signals and to detect when one or more of these signals is outside a settable threshold value. A first embodiment of the present system detects the heartbeat, and using the detected heartbeat computes a heart rate. Life-threatening arrhythmias (LTAs) can therefore be detected on a body-worn monitoring device. Three methods are anticipated in the detection of a heartbeat: an ECG channel, the auscultatory (audio) channel, and/or the accelerometry channel.

In order to improve both the sensitivity and specificity of heartbeat detection, the audio channel is also preferably provided in addition to the ECG channel. This audio channel may also be used to detect other physiologic events, such as breathing. Alternatively or in combination with the audio channel and the ECG channel, the at least one accelerometer 54 may be used to detect mechanical motion on the body surface. The use of three or more channels, each with different measurement methods, will improve the overall reliability of the event determination but stay within the resource limits of the contained microcontroller 202.

The embodiment herein described includes only ECG sensing with regard to a specific patient-triggered event or events for purposes of triggering the respondent device(s) 40. At least one event detecting algorithm is stored within the microprocessor 202 of the personal status monitoring device 10 is set to high sensitivity, though preferably the system further relies upon additional signal processing and pattern recognition within each of the personal gateway device 20 and/or the central server 30 for true positive qualifications prior to finally triggering the at least one respondent device 40a, 40b. It should be readily apparent that new techniques in signal processing are anticipated. For example, the audio channel may also be used for the detection of certain catastrophic events, as would be of interest in a threatening environment such as the military. The addition of the accelerometry channel also provides the capability of measuring environmental events, for example, such as exercise, or perhaps more significantly, when the patient falls accidentally or otherwise. This latter feature is of specific interest in healthcare facilities where patient falls are a significant adverse event and are costly. The accelerometer 54 also may be used to detect high motion artifacts and be used to control filters on the ECG and/or audio channels or turn these channels off such that false alarms due to motion artifacts are not passed through to at least one of the respondent devices 40, 40b. It will be readily apparent that these and other sensor fusion methods are possible within the ambits of the overall system architecture as indicated by the capability for additional input channels described herein.

In addition to event detection, the herein-described personal status monitoring device 10 supports a periodic wireless beacon function that maintains a connectivity state with the overall system and allows for data to be telemetered. Generally and according to this embodiment, the beacon may be generated in two ways: either by the personal status monitoring device 10 in periodic fashion or in response to a specific request by the central server 30 or the personal gateway device 20. According to the present embodiment, the beacon is set preferably to a periodic pattern that allows overall systems maintenance at an optimized low power consumption using the radios that are contained in the monitoring device 10 and a personal gateway device 20a, b, c, respectively. It should be noted that a preferred goal of the herein described system is to produce an optimized battery life for the personal status monitoring device 10 that is equivalent to greater than ninety percent of the duration of a hospital stay or one week, which ever is longer. Additionally and according to another aspect of the invention, the periodicity of beacon patterns being transmitted can be programmed in order to encode the type of physiologic parameter that is being monitored by each personal status monitoring device 10. For example, an "ECG-only" beacon such as the present embodiment may have a preprogrammed repetitive rate of one beacon transmission about every 2 seconds, whereas a "respiration rate" beacon from a separate personal status monitoring device 10 may have a beacon repetition rate of one beacon transmission every 11 seconds. Other similar encoding schemes may also be used for the same purpose.

Fundamental to low power consumption goal of the present invention is that it is intended that only primitive physiologic data such as R-R intervals, (in the case of ECG electrodes) battery status, and other high level indicators of either physiologic or device data are preferably embedded for periodic transmission within the beacon.

The beacon is generated by a low-power transceiver, preferably standards-based, using, for example, 802.15.4 standard (although it should be readily apparent that other radios with comparable performance can be substituted). As noted, this transceiver is normally and predominantly in the "OFF" state. That is, the sensor continuously detects on the patient, but the beacon only transmits at its programmed intervals to the personal gateway device in "normal" state in which the network is predominantly off.

At least one indicator can be optionally provided with each personal status monitoring device 10. To that end, an LED or LCD status indicator can be used to determine whether the monitoring device 10 is operational and whether the communication link with the personal gateway device 20 is active. In addition, the status indicator can also indicate by visual means whether context management (e.g., binding of the continuous physiologic signal, hardware ID 209, 524, FIG. 4, and the unique patient identifier 206) has been established or is being maintained. In lieu of or in combination with a visual means, an audio transducer, such as at least one of an LED and/or LCDs, can also be used. Each of these indicators may also be used to annunciate alarm conditions.

More particularly and in terms of overall signal processing, the personal status monitoring device according to this embodiment performs the following tasks. Each of the following tasks relate to the specific embodiment, wherein event detection is only triggered based on ECG measurement as the primary physiologic parameter.

i) Heart beat detection, based on the detection of an ECG QRS complex. As noted above, an additional acoustic channel may be employed in the personal status monitoring device 10 of the present embodiment to detect cardiac sounds;

ii) Heart rate or R-R interval measurements;

iii) Programmable high/low heart rate threshold crossing;

iv) Event detection, such as VTACH, Vfib, asystole;
v) Heart rate variability detection, for example, atrial fibrillation;
vi) Motion or patient activity detection using the accelerometry channel; and
vii) pacer detection.

In addition, data compression is also performed in the personal status monitoring device 10 in order to preserve the RF power, preferably using a non-linear data compression scheme, though others could be similarly contemplated. A beat detector can be used such as those commonly known in the field to a matched filter (MF) that operates on the sampled data in order to determine heartbeats and fiducial points. The fiducial points are used in order to bracket the PQRS complex and to determine the R-R interval. These intervals can then be compressed by means known to those skilled in the field.

Waveform data can also be compressed. ECG signal data is sampled at an appropriate Nyquist rate (e.g., 200 s/s). The extracted waveform beat is then compressed, using lossy or lossless compression techniques. The resulting compressed ECG sensor data is assembled in a packet for transfer across the RF link either in the beacon or on a periodic basis depending on the tradeoff of microcontroller power consumption for data compression versus RF section power consumption for transfer to the personal gateway device 20. Similar data compression schemes may be applied to other physiologic sensors.

With regard to the linkage between the personal-status monitoring device 10 and the intermediary personal gateway device 20, it is further noted that the personal gateway device 20 is linked bidirectionally according to this embodiment, to the central server 30 as described in greater detail below. Preferably and among other advantages, this linkage permits the personal status monitoring device 10 to download at least one program library from the central server 30. This downloading capability allows the microprocessor 202 of the personal status monitoring device 10 to be programmed with the most recent algorithms, for event detection, signal processing, data compression, etc., that are available to the central server 30, for example, upon connection to the patient or alternatively upon demand.

As noted and shown in FIG. 2, the personal status monitoring device 10 wirelessly communicates over the low-power (WPAN) network 24 with the personal gateway device 20a, 20b, 20c via a low cost, low power, preferably standards-based transceiver, using, for example, the IEEE 802.15.4 standard (although it should be readily apparent that other radios can be substituted). Data display, trend storage, additional signal processing and wireless relay of data originally transmitted to the gateway device by the personal status monitoring device subsequently to the central server 30a, 30b are tasks that are preferably performed by the personal gateway device 20a, 20b, 20c which is now described in greater detail.

At the outset, the personal gateway device 20a, 20b, 20c is also preferably designed to be embodied in a number of form factors, for example, and as noted a PDA, cellular phone, or other suitable design, such as a patient-worn version, depending, for example, on market attractiveness and other factors. The personal gateway device 20 preferably contains a compatible transceiver to that contained within the personal status monitoring device 10 for permitting bi-directional communication therewith over the personal area network 24.

According to the present embodiment, the personal gateway device 20 also preferably performs additional signal processing and statistical analysis in order to qualify events that are received from the personal status monitoring device 10 as true positive event candidates. True positive event candidates, as qualified by the personal gateway device 20, subsequently are relayed to the central server 30a through a medium or long range bi-directional wireless link 28a, 28b, preferably standards based, such as, for example, IEEE 802.11x for medium range 28a or alternatively any suitable cellular phone standards 28b. The gateway personal device 20 further provides a periodic beacon via a contained WLAN/WAN transceiver or radio in order to maintain connectivity with the central server 30. The intermediary gateway device 20 of this embodiment has greater power resources than the personal status monitoring device 10 and therefore permits greater data storage prior to accessing the server via an access point (not shown) of the network 28a, 28b. Therefore, the gateway device 20 serves as a buffer prior to transmission of same to the central server 30. As in the preceding, the beacon maintains network connectivity of the herein described system in which the state of the system is normally and predominantly "off" with the exception of the periodic beacon transmissions in spite of the fact that the sensors on the patient status monitoring device are continually monitoring the patient. For example, the beacon rate of the personal status monitoring device 10 can be on the order of about one transmission for each 5 seconds in which a transmission length is about 0.2 seconds and the personal gateway device 20 may have a beacon transmission rate of about one transmission every two minutes to the central server in which the transmission length is about 0.5 seconds. The preceding periods are provided to give the reader the overall impression of the normal "quiet" state of the herein described system.

In addition to the above features, a separate location radio 550 provides an additional beacon to a separate wireless infrastructure, such as is provided by Radianse Corp. or similar technology. This separate beacon provides a redundant means for transferring patient data information to the central server 30 and establishing network connectivity in a predominantly "off" or "quiet" state.

Referring to FIGS. 2 and 4, a primary function of the personal gateway device 20 is to act as a radio relay repeater from the personal status monitoring device 10 to the central server 30 through an intermediary RF link. In the case of in-building use by the system, an IEEE 802.11x radio technology is preferably utilized. WiFi (IEEE 802.11b) is preferred at the present time due to the overall pervasiveness of this radio standard in healthcare IT settings. As IT organizations may migrate to other standards based radios, such as IEEE 802.11(a) or (g) however, it will be readily apparent that other device configurations can alternatively be used. In the case of out-of-building use, the intermediate radio of the personal gateway device 20 is preferably based upon available cellular phone technologies, such as GSM, TDMA, CDMA, or G3, depending on local availability and coverage. Additionally, the personal gateway device 20 also preferably provides interim signal processing, pattern recognition, status indication and user actuation. The interim signal processing is provided preferably in a distributed manner relative to the sensitivity of the personal status monitoring device 10. By that, it is intended that the sensitivity of the processing of the gateway device 20 will eliminate additional false positives that were not eliminated by the personal status monitoring device 10.

As noted, the physical shape and mechanical design of the intermediary personal gateway device 20 is intended to assume a variety of multiple forms; for example, a neck-worn pendant, a badge form factor attached to a hospital gown, a clothing attachable tag, or a wrist worn bracelet, among others, the device in any event being configured for attachment to the patient with the overall design preferably being fairly simple and easy to utilize. Preferably, the wearability of the device 20 is modeled around that of long-term wear jewelry. In addition, the overall design of the personal gateway device 20 is durable as conventional monitors, is disinfectable, and is able to be worn by the patient, for example, in a shower. As with the personal status monitoring device 10, the personal gateway device 20 is preferably programmed with a unique (hardware) identification number 524, FIG. 4, that is stored in a non-volatile memory device 522, FIG. 4, and is preferably also denoted on the exterior surface of the device 20, preferably in at least one of a barcode and/or human-readable form.

The personal gateway device 20 of the present system has at least three primary functions, namely: to serve as an embedded radio coordinator, to serve as a secondary signal processor with regard to physiologic data, and further to provide a primitive information display as well as act as an input device. The personal gateway device 20 is preferably powered by either disposable or rechargeable batteries.

Referring to FIG. 4, a schematic diagram is provided wherein a plurality of contained transceivers or radios 500, 530, 540, 550 permit the relay of information between one another in a coordinated method through a contained microcontroller 520. These radios 500, 530, 540, 550 may contain one or more semiconductor chips. It should be readily apparent that additional radios or other wireless communications mean, such as for example, IrDA means, may be added to the present design. Furthermore, the microcontroller 520 may be embedded in one or more of the radios 500, 530, 540. These radios may also be combined integrally as silicon components become available.

The outputs of the radios 500, 530, 540, 550 are coupled to antennas 501, 531, 541, 551 respectively. These antennas 501, 531, 541, 551 may be combined to fewer structures in the case where the same spectrum is used by more than one radio. Parts or all of the radios 500, 530, 540, 550 may be combined where they share design similarities.

The embodiment illustrated in FIG. 4 provides communication relays between a WLAN radio 500 based on IEEE 802.11, (a), (b), or (g), depending on the facility infrastructure, in which the radio operates and the Personal Area Network 24, FIG. 2. Selected radios may contain more than one of these standards. An alternative radio for out of building use is based on WAN technologies, such as TDMA, CDMA, GSM, or G3 depending on local service provisions.

WPAN radio 530, according to this embodiment, provides two-directional communications between one or more personal status monitoring devices 10 to and from other devices connected through radios 500 and 540. Alternate radios, for example, such as those found in devices manufactured by Fitsense, Corp. may be substituted. In addition, an ultra short-range radio 540 is provided in order to read an RFID tag (not shown) attached to the patient, the tag containing demographic or other patient-related information. Other short range, non-standards based radios may also be utilized for this purpose.

Power management for the personal gateway device 20 is represented by components 511-513. The personal gateway device 20 preferably includes a rechargeable battery 513 having a useful life of over 5 days, or approximately equivalent to that of an average expected patient length of stay in a hospital. Longer battery life is highly desirable. Charging means is provided through a power supply circuit 512 that generates DC power from RF power, AC mains, or by harnessing mechanical, body thermal, or solar power 511 as is found for example, in digital wristwatches and known to those skilled in the art. Alternatively, a separate charging mechanism can be employed as commonly known to those of sufficient skill in the field. Power supply 512 regulates charging of the battery 513 and supplies power requirements to the components of the personal gateway device 20. Preferably, the battery 513 can be recharged to full storage in less than eight hours (e.g., overnight) when charged by AC mains or is trickle charged at a rate higher than power dissipation when harnessing other power sources.

A microcontroller 520 provides routing control of radios 500, 530, 540, 550 secondary signal processing and pattern recognition, and user interface through a display 529 that can be optionally provided with the device. In addition, at least one audible annunciator 527, and one or more visible indicators, such as LEDs 528, which may be combined with the audible annunciator 527, and one or multiple input actuators 525 to provide local alarm notification, as well as to provide an indication of connectivity status, and in the case of the visual display, patient identification, messaging from the central server 30 and personal status monitoring device 10. Display 529 may be used to display physiologic data from the sensors of the monitoring device 10. It will be appreciated that some or all of the above user interfaces can be implemented into the personal gateway device 20. Preferred embodiments may further include an audio and visible annunciator means only. The audible annunciator 527 is preferably required for the personal gateway device 20 to provide alarm annunciation in proximity to the patient (e.g., in the event the personal status monitoring device 10 does not have any alarm annunciation capability or in the instance that an alarm event occurs and the personal gateway device 20 loses communication with the central server 30).

The contained microcontroller 520, according to this embodiment, has an associated volatile memory device 521 and a non-volatile memory device 522. Preferably embedded in non-volatile memory device 522 at the time of manufacture is a unique identification number 524. Patient identification at the time of initially synching the device in connection with the personal status monitoring device 20, can be stored in non-volatile memory device 522 through any available input, such as, for example, manually by means of a barcode reader (not shown) or other suitable means, that can be utilized or biometric input 545. According to the present invention, the later obtained unique patient identifier 206 remains stored for as long as there is positive confirmation of connectivity to at least one of patient connected personal status monitoring device 10 and the device is receiving continuous patient data (at least one continuous physiologic signal); that is to say, the personal status monitoring device 10 remains attached to the patient, the device remains powered, etc. in a binding manner as previously noted in connection with the personal status monitoring device 10, thereby providing patient context management.

The microcontroller 520 of the personal gateway device 20 further preferably includes software in order to perform tasks that are specific to the system function. According to a preferred embodiment, these applications are written in applications modules (using, for example, Java script) that permit easy downloading of same from the central server 30a, 30b. These applications include, for example, encryption and authentication software that secures and protects patient confidentiality of data.

Figure 5:
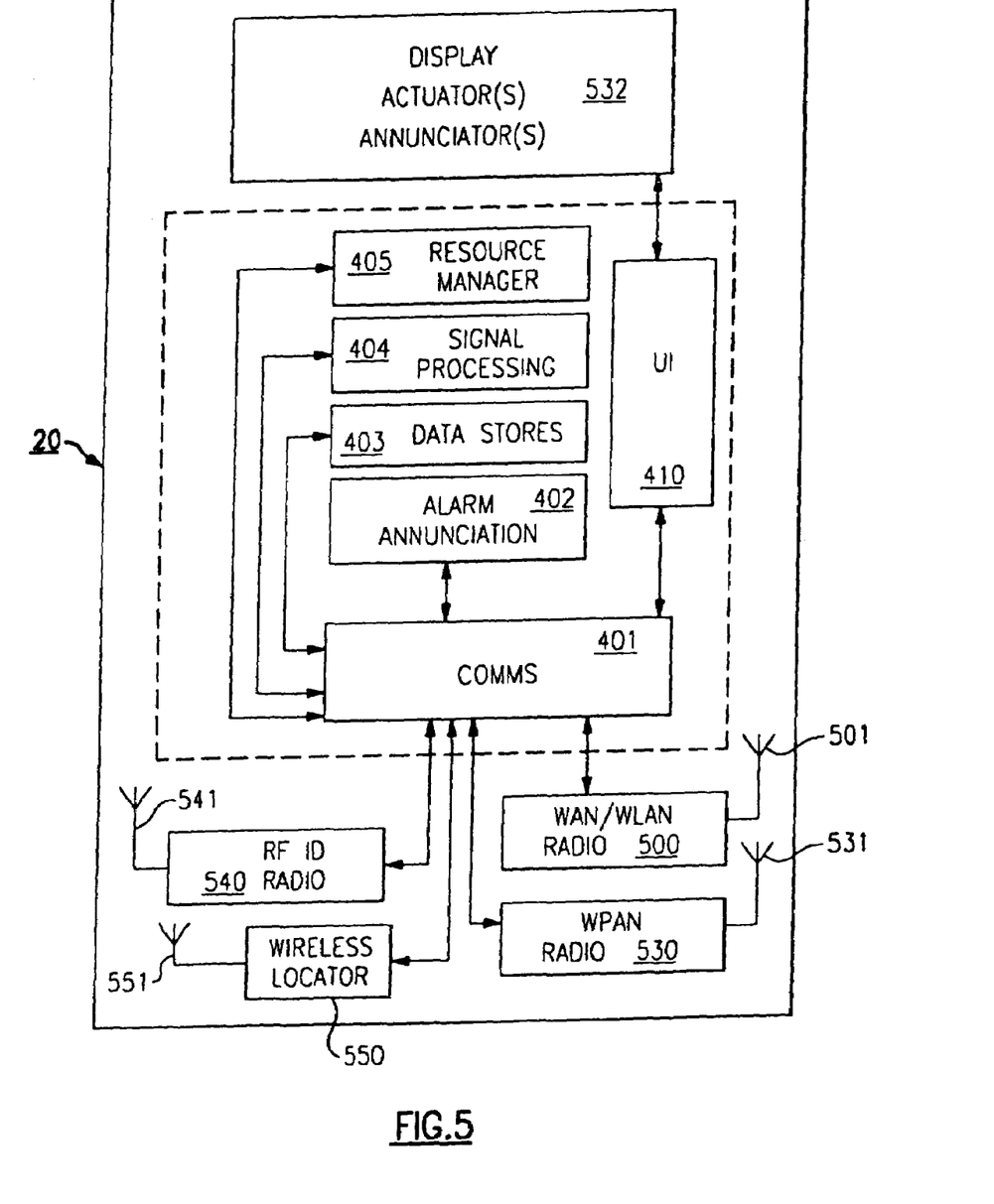
FIG. 5 is a schematic software diagram of the personal gateway device of FIG. 4.

A preferred embodiment of the software architecture for the personal gateway device 20 is illustrated in FIG. 5. It should be noted that the present architecture is exemplary and that other architectures known to those skilled in the art that achieve the same function may be substituted. Software coordination is organized and then is coordinated through a Comms Object 401.

Signal Processing Object 404 receives data from any of networked personal status monitoring devices 10 through the WPAN radio 530 and performs intermediate signal processing and pattern recognition. The primary purpose of the Signal Processing Object 404 is to provide further qualification of events that have been initially triggered by the personal status monitoring device 10 in order to reduce the incidence of false alarm events from passing onto the central server 30 through WAN/WLAN radio 420 and thereby reduce power consumption of the battery 513 that is contained in the personal gateway device 20. The intermediate signal processing optimizes the normal and predominant "off" state of the interconnected network by determining and controlling periodic beacon events between the personal gateway device 20 and the central server 30, which further reduces power consumption of the personal gateway device. Power management for the personal gateway device 20 is controlled through Resource Management Object 405, which also manages other resources, such as, but not limited to, microprocessor sleep status, task execution and priority, internal diagnostics and other resources.

Events are displayed or annunciated through UI object (user interface) 410 for local alarm and/or alerts through rules that are provided in Alarm Annunciation object 402 or from the server 30. Alarm Annunciation object 402 determines the priority of alarm and alert events, duration of annunciation and targeted annunciator (audible, visual, display, combination, and other) shown as 532.

Data from various internal and external sources are stored in the personal gateway device 20 through Data Stores Object 403. This data includes, but is not limited too, beacon patient data, event storage, including a snapshot of any raw physiologic waveforms, the last "N" events, where "N" is user-selectable, journaling data captured by the personal gateway device 20, and other suitable data relating to the patient to which the gateway device is connected, as well as local performance data.

Radio modules 500, 530, 540, 550 communicate with Comms Object 400 through Applications Program Interfaces (API) to Comms Object 401 to route data to other Objects. It is generally understood that the WPAN radio 530 provides connectivity to one or more personal status monitoring devices 10, the RFID radio 540 provides connectivity to a patient worn identification tag device. The WAN/WLAN radio 500 provides connectivity to the central server 30 and the wireless location radio 550 provides location capability and additional context management that relates the condition of the patient provided by one or more sensors to the environmental location of the patient. For example, location radio 550 may determine whether a patient is in a hospital bedroom or procedures room. This context data can be used to associate with specific patient care plans.

According to this embodiment, the central server 30a, 30b performs the functions of device management, providing rules sets or engines for the distribution and escalation of messages and data transfer to the respondent devices 40a, 40b, database management, client display rendering, interface in Clinical Information Systems (CIS) or Electronic Medical Records (EMR), web hosting of data, final determination of true positive events, indoor location mapping, and other software activities that may require greater processing power, storage or communications that is not possible in either the personal status monitoring device 10 or the personal gateway device 20. Interface to a known central monitoring station, such as, for example, the Acuity™ monitoring station manufactured by Welch Allyn, Inc. is preferred in that this interface allows the integration of the presently described Monitoring Networks and devices in such a way that the systems complement each other. However, an interface to a physiologic monitoring station is not a necessary requirement. The central server 30a, including its database 30b, is architected to be low cost in its minimal configuration, yet is scalable as devices and applications expand.

The hardware of the central server 30 is preferably based on the most cost effective yet scalable hardware platform. Intel based personal computers are a primary candidate due to cost. Linux is a primary operating system (OS) candidate for similar cost considerations. However, other hardware and software operating systems will be considered if they offer a cost effective alternative or there are other business compelling reasons to consider.

The central server 30 is preferably a low cost entry platform that is relatively easy to manufacture, configure and install. Preferably, the central server 30 includes graphical user interfaces (GUIs) that can utilize existing customer desktop computers running, for example Microsoft (OS) and having accessible web browsers.

The central server 30 also preferably includes an optional interface to an existing central monitoring station, such as, for example, the Acuity monitoring Station manufactured by Welch Allyn, Inc., serving as an installed base wherein the server offers features that link the respondent devices to the installed base as well also preferably offering a mobile patient ID.

The central server 30 also preferably supports mobile computing platforms, such as select mobile phones, PDAs running Microsoft or Palm OS that support extensible interfaces, such as, for example, compact Flash.

As to the task specifics handled by the central server 30, the central server is responsible for management of patient names/identifications and respondent device assignments. The central server 30 also acts as a repository for patient data storage as transmitted, either by the periodic beacon of the personal gateway device 20, by event transmission, and/or through specific request. This data can be stored preferably for a predetermined time (e.g., 10 days), the data typically including static waveforms and numeric data as conveyed originally from the personal status monitoring device 10, though compressed continuous data can also be stored depending on the extent of data compression in the device 10, as noted previously.

The central server 30 according to the present embodiment can also provide alarm annunciation, for example, either through a textual display of alarm or alert event with a segment of waveform displayed and/or audible signals or both.

Tabular or graphical trends can be displayed or outputted using the central server 30 in a manner that is similar or equivalent to those found, for example, on central stations such as the Acuity central monitoring station manufactured by Welch Allyn, Inc. In addition, the server 30 can also preferably provide output via print capabilities on any connected PCs or separate peripheral device.

In terms of output, a static ECG waveform (not shown) can be displayed by the central server 30, if supported by the personal status monitoring device 10. Preferably, the server 30 also maintains separate interfaces to Clinical Information Systems (CIS) or Electronic Medical Records (EMR) warehouses and is extendable to support other wireless products.

Display rendering on the respondent device 40 is preferably downloadable from the central server 30 using, for example, Java beans, applets, or other suitable software transfer methods. Data is transferred preferably to the respondent device 40a, 40b using XML with suitable data types and style sheets, though other software means may also be used as is generally known to one skilled in the field.

As has been noted throughout this discussion, battery operating time is an important consideration of the herein described system. Furthermore, and in the case of respondent devices that comprise either a PDA or a cellular phone, the ability to wake up and pre-empt other applications upon receipt of a message is an important design consideration. Therefore, an alarm message will take priority over applications in use or the at least one respondent device 40a, 40b at the time an alarm message is received. It is recognized that PDA operating systems must be considered as well. Preferred features of the respondent device(s) 40 include the following:

The respondent devices 40a, 40b according to the present embodiment each provides means for user (nurse, physician, etc.) authentication in order to access patient-related data (to satisfy standards such as HIPPA). In addition, the respondent device 40a, 40b includes a graphical user interface that allows entry of patient-related data over the bi-directional link into the personal status monitoring device 10.

The respondent device 40a, 40b according to this embodiment includes a patient context manager. This context manager communicates with the personal status monitoring device 10, via a network (in order to perform binding and context management). The manager admits, initiates, personal status monitoring device patient ID and other unique patient context fields, and views patient context. The respondent device 40a, 40b also preferably includes a clinical administrative manager. This manager includes a register respondent responsible for patients and allows acknowledgment of alarms.

A personal status monitoring device data display indicates patient ID, name, current data, patient location, stored data in columnar tabular format as well as an alarm condition (auto open) with current numerics and sampled waveform (if available from the personal status monitoring device).

It will be readily apparent that the above features of the respondent device 40a, 40b can be expanded with the addition of parameters, as new patient status monitoring devices are conceived (for example NIBP, pulse oximetry). Expansion of the graphical user interface is an improvement well within the intended purview of the invention.

The software architecture of the respondent device 40 is relatively simple. Regardless of the platform, the at least one respondent device 40 is essentially a lightweight client whose primary purpose consists of two activities:

First, the respondent device 40 is intended to display information transmitted to it by the central server 30, including alarm annunciation via speaker and data display on the respondent device. Secondly, the at least one respondent device 40 is intended to read and transmit clinician input back to the central server 30.

All of the functionality of the respondent device 40 noted in the previous section falls into one of these categories, and can be carried out using an appropriately equipped browser that is preferably provided on the respondent device 40a, 40b or other suitable means known to those skilled in the art.

This lightweight implementation shifts the burden of data acquisition and formatting from the respondent device 40a, 40b onto the central server 30, from which the respondent device obtains its information.

Figure 6:
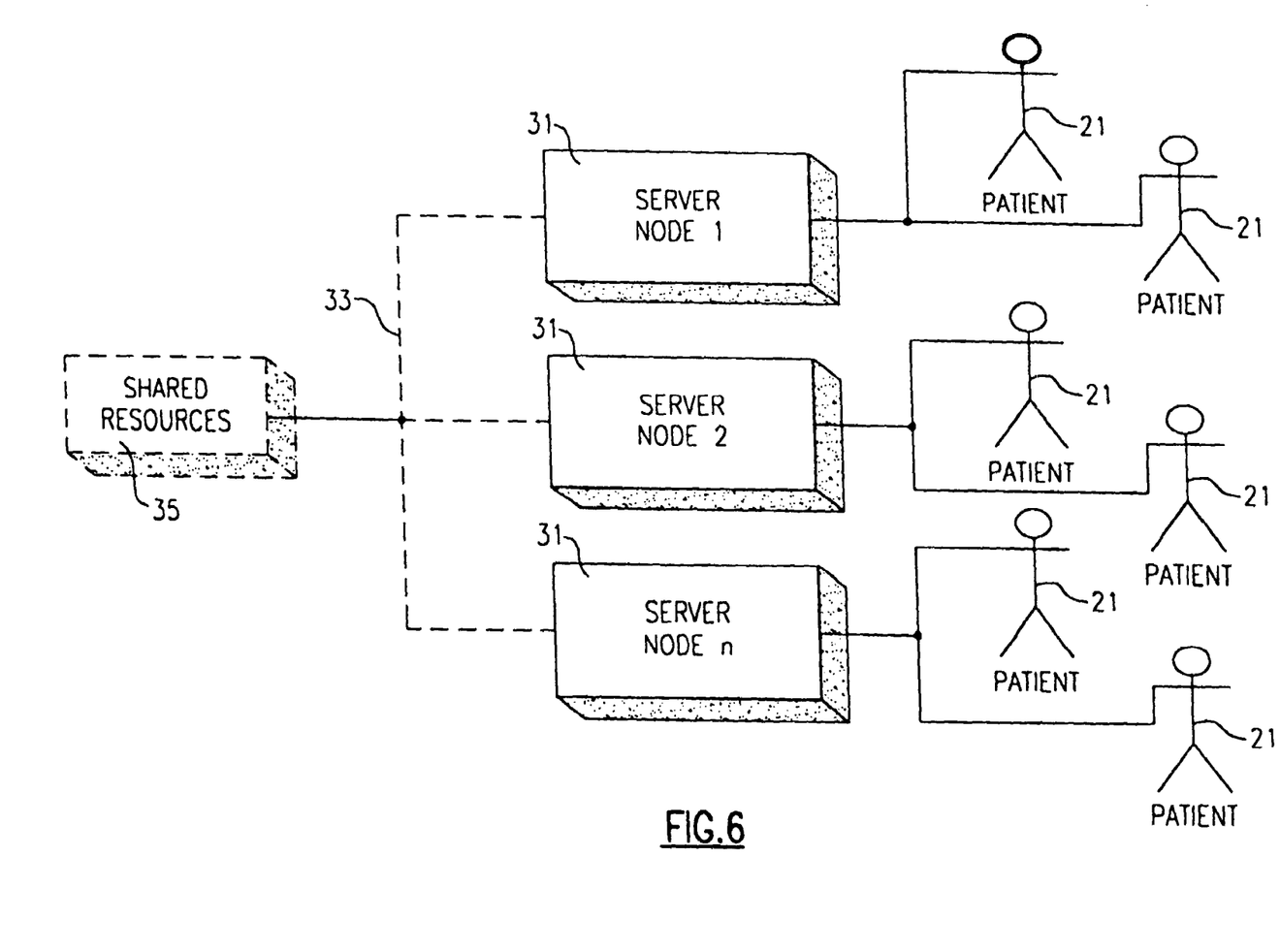
FIG. 6 depicts a schematic diagram employing the presently described system as used in a health care facility or similar environment.

It should be apparent that there are other variations and modifications that are possible within the intended scope of the invention. One possible network configuration is illustrated in FIG. 6, wherein a number of patients 21 are configured, each with monitoring devices (not shown), that are connected via the personal network (WPAN) to a respective gateway device (not shown). Each of the gateway devices is connected to a server node 31, serving the overall functionality of the central server discussed previously. In this instance, a plurality of server nodes 31 are disposed in order to increase capacity. This configuration would be particularly useful in those environments in which a large number of patients 21 are to be monitored. For purposes of this description, "N" number of server nodes 31 are provided, each server node being configured for handling a block of patients 21.

For example, a set of patients (e.g., beds), each being equipped with body-worn patient status monitoring devices 10, FIG. 1, and intermediary (e.g., gateway) devices 20, FIG. 1, as described above, or a hospital floor having a predetermined number of patients with same would be assigned to a specific server node 31, wherein the assigned server node would monitor those patients (with regard to event detection). If the load increases, additional server nodes 31 could be added to handle this block of patients. In this manner, the system scales in order to more effectively handle a greater number of patients. Optionally, any or each of the server nodes 31 of the herein described system could also work cooperatively, as shown by line 33, thereby sharing data or other resources 35 as needed. The shared resources 35 can include, for example, nurse/caregiver assignments, printers, and an HIS/CIS interface, among other resources.

With the preceding background and detail concerning the above system and its architecture, the following use case scenario herein summarizes one intended functionality and purpose of the described system as depicted in FIG. 2. A patient experiences chest pains and is transported to a hospital emergency department. Upon arrival at the emergency department, a clinical technician places a patient status monitoring device 10 on the patient's body over the left chest (e.g., over the heart) and straps a personal gateway device 20a on the patient's arm. The patient status monitoring device 10 nitiates linkage to the personal gateway device 20a via the PAN 24 and upon completion of linkage, indicators 107, FIG. 3, and 528, FIG. 5, respectively, display successful communications have been established therebetween. The patient status monitoring device 10 simultaneous to its linkage with the personal gateway device 20a, begins measuring and analyzing the patient's ECG and sending HR and R-R values to the personal gateway device 20a over a periodic beacon through the wireless PAN 24. The personal gateway device 20a in turn, communicates to the central server 30a through a Wireless Local Area Network (WLAN) 28a and establishes a database 30b of heartrate (HR) and R-R interval values.

In the meantime, the technician enters patient identification data and patient specific alarm settings into a respondent device 40a. Identification data and alarm settings are communicated to the central server 30a over the WLAN link 28a to the database 30b where a unique patient identifier 206 is assigned. Alarm settings and the unique patient identifier 206 are down loaded to the personal gateway device 20a over the WLAN 28a for storage in the gateway device and downloaded from the personal gateway device 20a for storage in the patient status monitoring device 10. Subsequent transmissions of beacons from the personal status monitoring device 10 and the personal gateway device. 20a to the central server 30a are embedded with the unique patient identifier 206, FIGS. 3, 4, and the hardware identifiers 209, FIG. 3, and 524, FIG. 4. Other embodiments may not need to append hardware identifies since this capability may be embedded in communication protocols, such as TCP/IP. The combination of the unique patient identifier 206, the separate hardware identifiers 209, 524, FIGS. 3, 4, respectively and the continuous detection of physiologic data causes the system between patient and the central server 30a to be "bound".

The herein described system operates in a normally off state. That is, beacons between the patient status monitoring device 10 and the personal gateway device 20a over the first wireless link/network 24, and second beacons between the personal gateway device 20a and the central server 30a over the second wireless network 28a are set to the longest possible interval, while maintaining a positive communication link between the patient status monitoring device 10 and the central server 30a in order to preserve battery energy of each of the patient status monitoring device 10 and the intermediary personal gateway device 20a. Care providers may view patient data from a variety of displays, including those provided on respondent devices 40a, 40b, or displays connected to the network such as laptops 6a, PCs 6b or printers 6c.

The central server 30a stores caregiver patient assignments and caregiver to respondent device assignments in the database 30b. Such assignments may be used to route patient data to specific respondent devices 40a, 40b. The central server 30a may contain rules sets that allow escalation of alarm notification in the case where the first or primary (assigned) respondent device 40a, 40b is not available within a prescribed time.

In the event that the patient experiences an alarm event, the patient status monitoring device 10 immediately communicates data, including but not limited to physiologic waveforms, cause of alarms and other pertinent data to the personal gateway device 20a. Signal processing 404, FIG. 5, further analyses data to reduce alarms caused by artifacts. True positive alarms are sent over the second wireless network (WLAN) 28a to the central server 30a. The central server 30a matches patient identifier with an assigned respondent and sends alarm data to a respondent device 40a over the second wireless link 28a. The central server 30a may communicate alarm to more than one respondent device 40a, 40b. The care giver may acknowledge the alarm via the respondent device 40a, 40b to silence or suspend the alarm.

Included in the system is a means for locating the patient status monitoring device 10, the personal gateway device 20a, and/or the respondent device 40a through a location device 550, FIG. 5. The location device 550, may also be embedded in the personal status monitoring device 10 and the respondent device 40a in addition to the intermediary device, as shown herein. Location device 550, FIG. 5, transmits a beacon to location receivers which are linked to the central server 30a. The central server 30a determines location coordinates or other location identification for communication to at least one respondent device 40a, 40b. In the event of an alarm, location information is sent to the respondent devices 40a, 40b. Similarly, the location device 550 can identify when the patient is transferred from one area of the hospital or other health care facility to another.

Upon discharge from the hospital, the patient can exchange the personal gateway device 20a which may be limited to a Wireless Local Area Network (WLAN) 28a with a personal gateway device, such as a programmable cellular phone 20c, that is capable of communication across a Wide Area Network (WAN) 28b. Furthermore, as know to those skilled in the art, the personal gateway devices 20a, 20c may have capabilities for both WLAN 28a and WAN 28b.

While the present invention has been particularly shown and described with reference to the preferred mode as illustrated in the drawing, it will be understood by one skilled in the art that various changes in detail may be effected therein without departing from the spirit and scope of the invention as described by the following claims.

We claim:

1. A method for communicating data over a network linking at least one respondent device with at least one battery-powered patient monitoring device, said method comprising the steps of:

continuously measuring at least one physiologic parameter for purposes of detecting a predetermined event using said at least one monitoring device;

storing continuously measured physiological parameter data into memory of said monitoring device;

operating said network in a quiet state in which said patient monitoring device transmits a periodic wireless beacon in order to continually maintain connectivity state with said at least one respondent device in which said predetermined event has not occurred; and transmitting said measured and stored data over said network in an active state only after said predetermined event has occurred, thereby saving battery power of said patient monitoring device.

2. A method according to claim 1, wherein connectivity is established over said network between an intermediary device and said patient monitoring device and between said intermediary device and said at least one respondent device, respectively.

3. A method according to claim 2, including the step of linking said intermediary device and said patient monitoring device over a first network and said intermediary device and said at least one respondent device over a second network.

4. A method according to claim 2, wherein said intermediary device transmits a periodic wireless beacon to establish connectivity with said at least one respondent device.

5. A method according to claim 4, wherein the period of said wireless beacon between said intermediary device and said at least one respondent device is not identical to the period of said wireless beacon function of said patient monitoring device.

6. A method according to claim 2, wherein said intermediary device is body-worn.

7. A method according to claim 2, including the additional step of processing said sensor data at said patient monitoring device prior to transmission to determine if said predetermined event has occurred.

8. A method according to claim 7, including the additional step of further processing received data from said patient monitoring device at said intermediary device prior to transmission to said at least one respondent device to verify said predetermined event has occurred.

9. A method according to claim 8, wherein said intermediary device transmits said data to said at least one respondent device only if predetermined event has been verified during said additional processing step.

10. A method according to claim 8, including a server that receives data transmitted from said intermediary device prior to said at least one respondent device, said method including the additional step of further processing data received from said intermediary device prior to transmitting said data to said at least one respondent device to verify said predetermined event has occurred.

11. A method according to claim 8, including the step of providing a first level of signal processing at said patient monitoring device and a higher level of signal processing at said intermediary device.

12. A method according to claim 1, wherein said predetermined event includes a threshold of at least one physiologic parameter.

13. A method according to claim 1, wherein said patient monitoring device is body worn.

14. A method according to claim 1, wherein a portion of said continuously measured data is included in said periodic beacon.

* * * * *